(12) United States Patent
Lee et al.

(10) Patent No.: US 10,058,862 B2
(45) Date of Patent: Aug. 28, 2018

(54) MICROFLUIDIC DEVICE

(71) Applicant: SAMSUNG ELECTRONICS CO., LTD., Suwon-si (KR)

(72) Inventors: Jong Gun Lee, Yongin-si (KR); Seung Hyun Kim, Anyang-si (KR); Seung Hoon Kim, Suwon-si (KR); Jung Ki Min, Yongin-si (KR); Yang-Ui Lee, Hwaseong-si (KR); Jae Sang Noh, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 519 days.

(21) Appl. No.: 14/632,327

(22) Filed: Feb. 26, 2015

(65) Prior Publication Data

US 2015/0238955 A1 Aug. 27, 2015

(30) Foreign Application Priority Data

Feb. 26, 2014 (KR) ........................ 10-2014-0022876

(51) Int. Cl.
*B01L 3/00* (2006.01)
*B01L 99/00* (2010.01)
(Continued)

(52) U.S. Cl.
CPC ..... *B01L 3/502715* (2013.01); *B01L 3/50273* (2013.01); *B01L 3/502738* (2013.01);
(Continued)

(58) Field of Classification Search
CPC .............. B01L 3/00; B01L 99/00; G01N 1/10
USPC ........ 422/50, 68.1, 502, 503, 504, 537, 547, 422/550, 554, 551, 552, 553; 436/43, 436/174, 180
See application file for complete search history.

(56) References Cited

U.S. PATENT DOCUMENTS 6,124,138 A * 9/2000 Woudenberg ......... B01L 3/5027
435/287.2
6,527,003 B1 * 3/2003 Webster .................... F15C 5/00
137/15.18
(Continued)

FOREIGN PATENT DOCUMENTS

KR  10-2011-0088746 A  8/2011
KR  10-2011-0120790 A  11/2011
KR  10-2012-0080765 A  7/2012

*Primary Examiner* — Brian J Sines
(74) *Attorney, Agent, or Firm* — Sughrue Mion, PLLC

(57) ABSTRACT

Disclosed herein is a microfluidic device, which includes a platform, at least one chamber provided in the platform to accommodate a sample, and at least one channel configured to couple the chambers to each other. The at least one chamber includes a detection chamber configured to detect the sample, and the microfluidic device further includes a light blocking portion configured to prevent external light from entering the detection chamber so as to prevent occurrence of errors in detection of the sample in the detection chamber. The microfluidic device can be useful for preventing the occurrence of detection errors which might otherwise be caused by interference of external light. The microfluidic device may also be useful for reducing an inspection time and for miniaturizing microfluidic devices. Further, the microfluidic device may be useful for preventing contaminants from entering the detection chamber.

7 Claims, 6 Drawing Sheets

(51) Int. Cl.
*G01N 1/10* (2006.01)
*G01N 21/07* (2006.01)
(52) U.S. Cl.
CPC ........ *G01N 21/07* (2013.01); *B01L 2300/021* (2013.01); *B01L 2300/069* (2013.01); *B01L 2300/0806* (2013.01); *B01L 2400/0409* (2013.01); *B01L 2400/0677* (2013.01); *B01L 2400/0688* (2013.01)

(56) References Cited

U.S. PATENT DOCUMENTS

| | | | | |
|---|---|---|---|---|
| 2010/0044918 | A1* | 2/2010 | Lee | B01L 3/502707 264/297.8 |
| 2010/0213063 | A1* | 8/2010 | Zenhausern | G01N 21/645 204/452 |
| 2010/0303687 | A1* | 12/2010 | Blaga | B01L 3/502738 422/504 |

* cited by examiner

MICROFLUIDIC DEVICE

CROSS-REFERENCE TO RELATED APPLICATION

This application claims priority from Korean Patent Application No. 10-2014-0022876, filed on Feb. 26, 2014 in the Korean Intellectual Property Office, the disclosure of which is incorporated herein by reference in its entirety.

BACKGROUND

1. Field

Exemplary embodiments relate to a microfluidic device, and more particularly, to a microfluidic device having an improved structure which is capable of reducing an inspection time and preventing occurrence of detection errors.

2. Description of the Related Art

A driving pressure is required to transfer a fluid in a microfluidic structure. Generally, a centrifugal force and a capillary pressure are often used as the driving pressure, and a pressure caused by a separate pump is often used as the driving pressure. In recent years, disk-shaped microfluidic devices, which have a microfluidic structure provided at a disk-shaped body thereof and thus use a centrifugal force to transfer a fluid and to perform a series of processes, have been proposed. Such a microfluidic device is referred to as Lab CD, a lab-on a disk, or a digital bio-disk (DBD).

Generally, a disk-shaped microfluidic device includes a chamber configured to store a fluid, a channel through which the fluid flows, and a valve configured to adjust a flow of the fluid, and may be constructed by using various combinations of these parts.

A microfluidic device may be used as a sample test device configured to test a sample such as blood, saliva, urine, or the like. A reagent which can react with a certain material in the sample is provided inside the microfluidic device. In this case, the sample may be tested by injecting the sample into the microfluidic device and detecting reaction results of the reagent with the sample.

In conventional microfluidic devices, a sample is weighed in a separate chamber, and a reaction of the sample occurs in a reaction chamber. Therefore, the conventional microfluidic devices have problems in that a separate chamber in which the sample weighing is carried out in a given space is required, and a relatively long inspection time is also characteristic.

In addition, impurities which are generated during a sample inspection may be introduced into the detection chamber, and/or external light may enter the detection chamber, resulting in occurrence of detection errors.

SUMMARY

Therefore, it is an aspect of one or more exemplary embodiments to provide a microfluidic device which is capable of reducing an inspection time and which is also capable of preventing an occurrence of detection errors.

Additional aspects of the exemplary embodiments will be set forth in part in the description which follows and, in part, will be obvious from the description, or may be learned by practice of the exemplary embodiments.

According to one aspect of one or more exemplary embodiments, a microfluidic device includes a platform, at least two chambers which include a first chamber which is provided in the platform to accommodate a sample and at least a second chamber, and at least one channel configured to couple the first chamber to the at least the second chamber. In particular, the at least two chambers include a detection chamber configured to detect the sample, and the microfluidic device further includes a light blocking portion configured to prevent external light from entering the detection chamber so as to prevent an occurrence of at least one error which relates to a detection of the sample in the detection chamber.

In this case, the light blocking portion may be arranged to surround an outer wall of the detection chamber.

The light blocking portion may be formed of a material that is impenetrable by light so as to prevent external light from entering the detection chamber.

The chambers may further include a quantitative reaction chamber configured to facilitate a simultaneous weighing of the sample and reaction of the sample.

A porous material may be arranged inside the quantitative reaction chamber so as to facilitate a combining of the sample with the porous material and then a weighing of the combination.

The microfluidic device may further include a contaminant accommodation chamber configured to accommodate contaminants generated as a result of the reaction of the sample in the quantitative reaction chamber.

The contaminant accommodation chamber may include an inlet port configured to facilitate a flow of the sample into the contaminant accommodation chamber, and an outlet port configured to facilitate a flow of the sample out from the contaminant accommodation chamber and into the detection chamber.

A distance between the outlet port and a central region of the platform may be shorter than a distance between a center of the contaminant accommodation chamber and the central region of the platform.

A distance between the inlet port and the central region of the platform may be shorter than a distance between the center of the contaminant accommodation chamber and the central region of the platform.

The at least two chambers may further include a waste chamber configured to accommodate an overflow of the sample which occurs after the detection chamber is filled.

The at least two chambers may further include at least one buffer chamber configured to accommodate a washing solution for washing a reagent which has reacted in the quantitative reaction chamber.

The microfluidic device may further include a valve provided on the at least one channel. The valve may include phase transition material and exothermic particles dispersed in the phase transition material.

The phase transition material may include at least one of a wax, a gel and a thermoplastic resin.

According to another aspect of one or more exemplary embodiments, a microfluidic device includes a platform, at least two chambers which include a first chamber which is provided in the platform and configured to accommodate a sample and at least a second chamber, and at least one channel configured to couple the first chamber to the at least the second chamber. In particular, the at least two chambers include a quantitative reaction chamber configured to facilitate a simultaneous weighing of the sample and reaction of the sample, and a detection chamber configured to detect a sample which has reacted in the quantitative reaction chamber.

In this case, a porous material may be arranged inside the quantitative reaction chamber so as to facilitate a combining of the sample with the porous material and then a weighing of the combination.

The microfluidic device may further include an accommodation chamber coupled to the quantitative reaction chamber and configured to accommodate the sample so as to prevent the sample from overflowing.

The microfluidic device may further include a first waste chamber configured to accommodate a remaining amount of the sample after the sample is quantified in the accommodation chamber.

The microfluidic device may further include a contaminant accommodation chamber configured to accommodate contaminants generated as a result of a reaction of the sample in the quantitative reaction chamber prior to a transferring of the sample to the detection chamber.

The contaminant accommodation chamber may include an inlet port configured to facilitate a flow of the sample into the contaminant accommodation chamber, and an outlet port configured to facilitate a flow of the sample out from the contaminant accommodation chamber and into the detection chamber, and a respective distance between each of the outlet and inlet ports and a central region of the platform may be shorter than a distance between a center of the contaminant accommodation chamber and the central region of the platform.

The microfluidic device may further include a valve provided on the at least one channel. The valve may include phase transition material and exothermic particles dispersed in the phase transition material.

The phase transition material may include at least one of a wax, a gel and a thermoplastic resin.

The contaminants may be generated as the valve is melted.

The microfluidic device may further include a light blocking portion configured to surround an outer wall of the detection chamber so as to prevent an occurrence of at least one error which relate to a detection of the sample in the detection chamber.

The at least two chambers may further include a second waste chamber configured to accommodate an overflow of the sample which occurs after the detection chamber is filled.

According to still another aspect of one or more exemplary embodiments, a microfluidic device includes a platform, at least two chambers which include a first chamber which is provided in the platform and configured to accommodate a sample and at least a second chamber, and at least one channel configured to couple the first chamber to the at least the second chamber. In particular, the at least two chambers include a reaction chamber in which a reaction of the sample occurs, a contaminant accommodation chamber configured to accommodate contaminants generated as a result of the reaction of the sample in the reaction chamber, and a detection chamber configured to detect the sample.

In this case, the sample may move via the at least one channel among the reaction chamber, the contaminant accommodation chamber and the detection chamber.

The contaminant accommodation chamber may include an inlet port configured to facilitate a flow of the sample into the contaminant accommodation chamber, and an outlet port configured to facilitate a flow of the sample out from the contaminant accommodation chamber and into the detection chamber A distance between the outlet port and a central region of the platform may be shorter than a distance between a center of the contaminant accommodation chamber and the central region of the platform.

A distance between the inlet port and the central region of the platform may be shorter than a distance between the center of the contaminant accommodation chamber and the central region of the platform.

The microfluidic device may further include a light blocking portion configured to surround an outer wall of the detection chamber so as to prevent an occurrence of errors which relate to a detection of the sample in the detection chamber.

The microfluidic device may further include a valve provided on the at least one channel. The valve may include phase transition material and exothermic particles dispersed in the phase transition material.

The phase transition material may include at least one of a wax, a gel and a thermoplastic resin.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
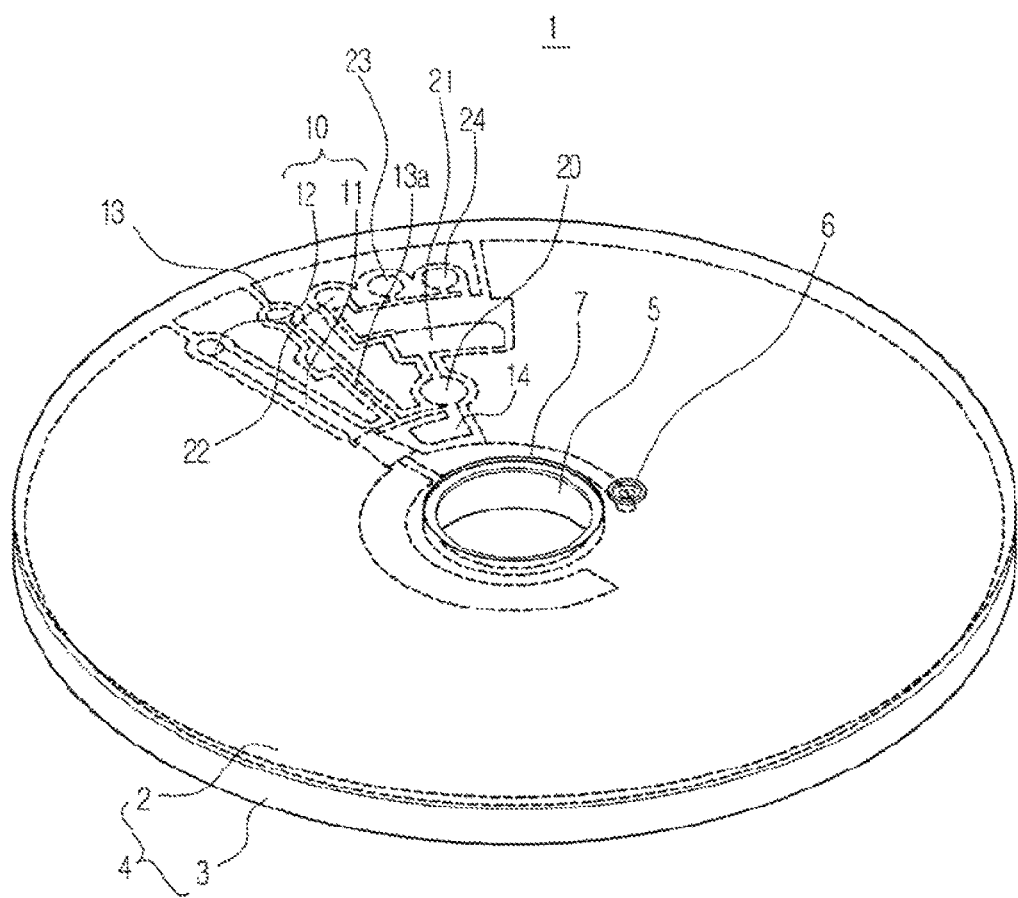
FIG. 1 is a perspective view showing a microfluidic device, according to one exemplary embodiment.

Reference will now be made in detail to exemplary embodiments, examples of which are illustrated in the accompanying drawings, wherein like reference numerals refer to like elements throughout.

Hereinafter, exemplary embodiments will be described in further detail with reference to the accompanying drawings.

FIG. 1 is a perspective view showing a microfluidic device, according to one exemplary embodiment.

As shown in FIG. 1, the microfluidic device 1 may include a rotatable disk-shaped platform 4, at least one chamber partitioned in the platform 4 to accommodate a fluid, and at least one channel through which the fluid flows. In addition, the microfluidic device 1 may include a bar code (not shown) which is provided at a lateral surface of the platform 4.

The platform 4 may rotate by using a central region 5 of the platform 4 as an axis of rotation. Movement, centrifugation and mixing of a sample in the chamber and the channel disposed in the platform 4 may be carried out by an action of a centrifugal force which is generated by rotation of the platform 4.

The platform 4 is easily moldable, and a surface of the platform 4 may be formed of a plastic material, such as, for example, any one or more of a biologically inert acrylic polymer, PDMS, PMMA, etc. However, various materials may be used for the platform 4, provided that the materials have chemical and biological stabilities and mechanical processability, but the present exemplary embodiment is not limited thereto.

The platform 4 may be composed of plates with a plurality of layers. A space and a passage may be provided in the platform 4 by forming a depressed or embossed structure which corresponds to a chamber or a channel on a contact surface in which the plates come into contact with each other and joining the plates together.

For example, the platform 4 may have a structure which includes a first substrate 2 and a second substrate 3 attached to the first substrate 2, or a structure including partition plates (not shown) configured to define at least one chamber which may accommodate a fluid between the first substrate 2 and the second substrate 3 and at least one channel through which the fluid may flow. In addition, the platform 4 may have various shapes. The first substrate 2 and the second substrate 3 may be made of a thermoplastic resin.

The joining of the first substrate 2 and the second substrate 3 may be performed using any of various methods, such as, for example, adhesion using an adhesive or a double-sided adhesive tape, ultrasonic fusion, laser fusion, etc.

Hereinafter, microfluidic structures disposed in the platform 4 will be described with respect to testing of a sample.

The sample may be prepared by mixing a fluid with a material in the form of particles having a higher density than the fluid. For example, the sample may include biological samples such as, for example, any one of blood, saliva, urine, etc.

An injection chamber 7 may be radially disposed at an inner side of the platform 4. The injection chamber 7 is partitioned to accommodate a predetermined amount of a sample, and a sample injection port 6 configured to inject a sample into the injection chamber 7 is formed at an upper surface of the injection chamber 7.

The entire sample may be used for inspection, for which the fluid is used in a state in which the fluid is mixed with the material in the form of particles. Further, a sample separation chamber 10 configured to centrifuge a sample by rotation of the platform 4 may be radially provided at an outer side of the injection chamber 7. The sample separated in the sample separation chamber 10 moves to a quantitative reaction chamber 20, and reacts while being quantified. Thereafter, the reacted sample moves to a detection chamber 23 via a contaminant accommodation chamber 22. Such movement of the sample will be described below.

Figure 2:
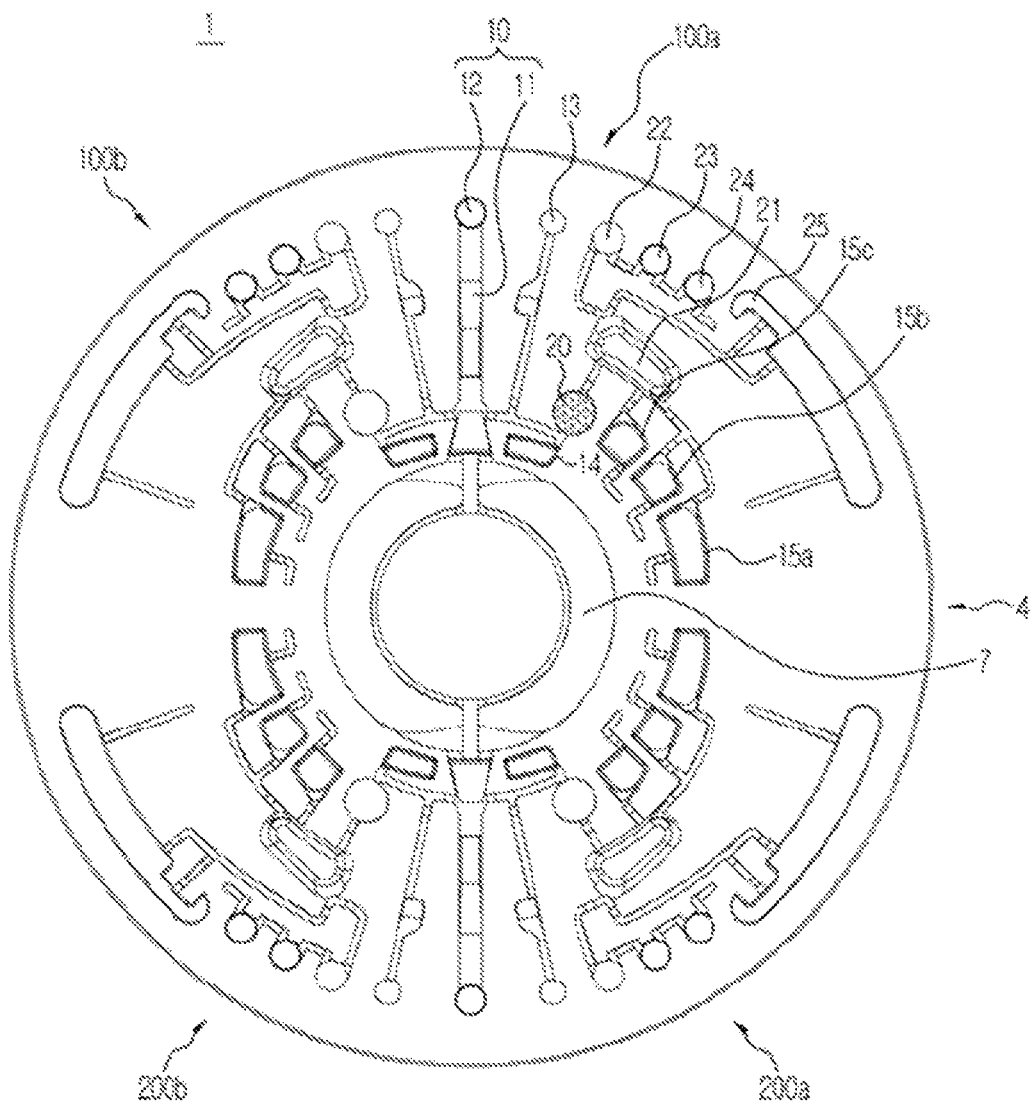
FIG. 2 is a plane view showing an entire configuration of the microfluidic device, according to one exemplary embodiment.
Figure 3:
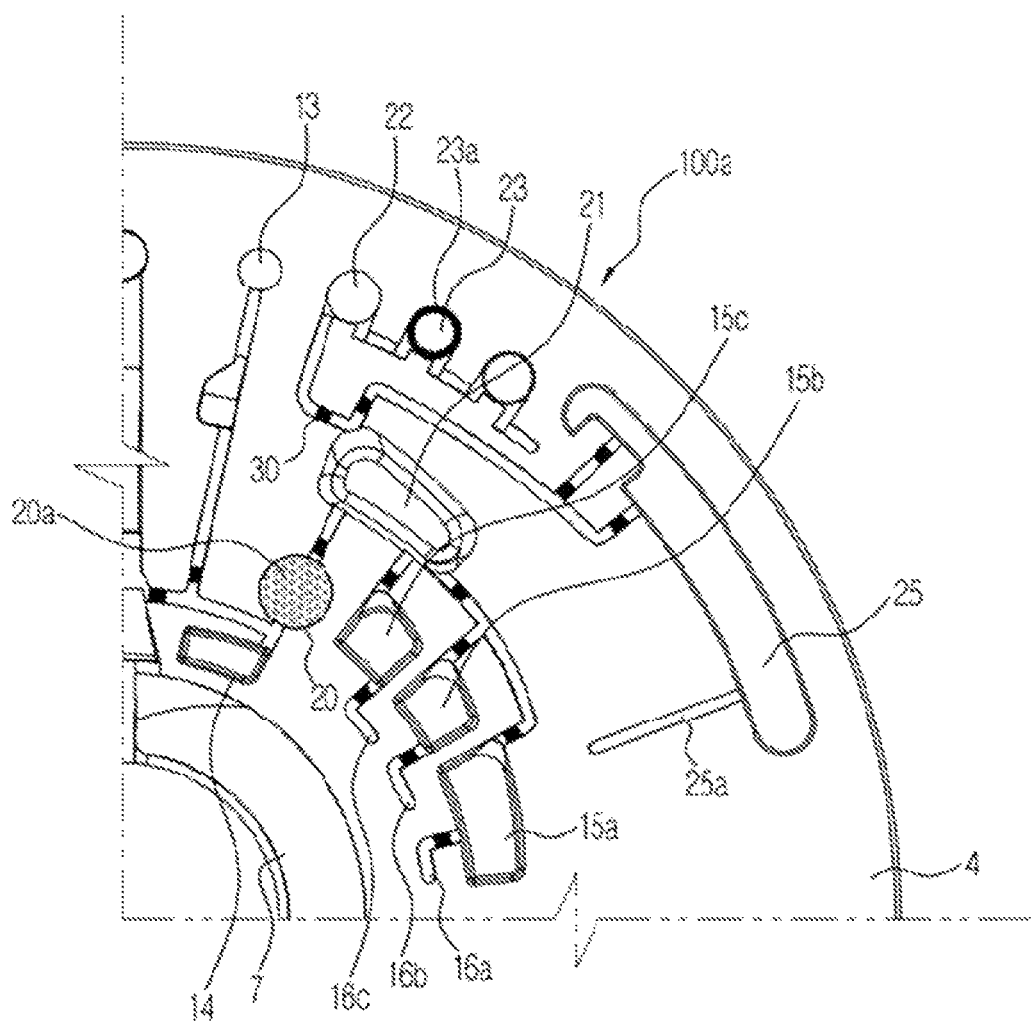
FIG. 3 is a diagram showing one unit from among a plurality of analysis units of the microfluidic device, according to one exemplary embodiment.
Figure 4:
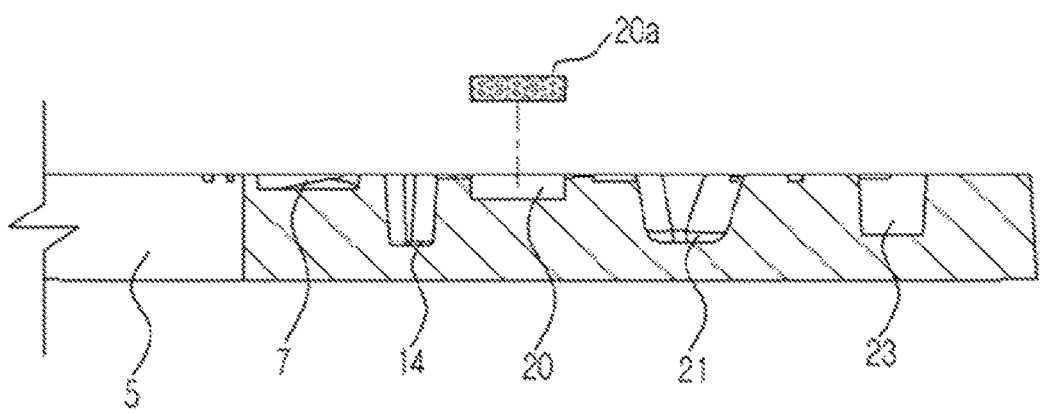
FIG. 4 is a cross-sectional view showing a cross-section taken along line AA' shown in FIG. 3.

FIG. 2 is a plane view showing an entire configuration of the microfluidic device according to one exemplary embodiment, FIG. 3 is a diagram showing one unit from among a plurality of analysis units of the microfluidic device according to one exemplary embodiment, and FIG. 4 is a cross-sectional view showing a cross-section taken along line AA' shown in FIG. 3.

As shown in FIGS. 2, 3, and 4, the microfluidic device 1 according to an exemplary embodiment may include a plurality of analysis units 100a, 100b, 200a, and 200b. As shown in the drawings, the microfluidic device 1 includes a total of four analysis units 100a, 100b, 200a, and 200b. The first analysis unit 100a and the second analysis unit 100b share a first sample separation chamber, and the third analysis unit 200a and the fourth analysis unit 200b share a second sample separation chamber. Therefore, it is possible to perform a plurality of inspections on one sample. Hereinafter, the first analysis unit 100a will be described as one example.

The sample injected into the injection chamber 7 is transferred to the sample separation chamber 10, and centrifuged by rotation of the platform 4. The sample separation chamber 10 may include a supernatant collection portion 11 in the form of a channel which radially extends outward from the injection chamber 7, and a precipitate collection portion 12 which is radially disposed outside the supernatant collection portion 11 in order to provide a space which is capable of accommodating a precipitate having a relatively higher specific gravity. When the sample is blood, blood cells are collected in the precipitate collection portion 12 as the platform 4 rotates, and sera are collected in the supernatant collection portion 11, the sera having a relatively lower specific gravity than the blood cells. Therefore, the blood is divided into the sera and blood cells in the sample separation chamber 10, and the sera are used for inspection.

Next, the sample is quantified at a predetermined amount required for inspection, and the sample flows into the quantitative reaction chamber 20 in order to react with a reagent. Weighing of the sample and reaction of the sample occur in the quantitative reaction chamber 20 at the same time.

Because of the presence of a porous material 20a which is accommodated into the quantitative reaction chamber 20, it is possible to perform the weighing and reaction of the sample simultaneously. Examples of porous material 20a may include any one or more of porous membranes, micropores, and/or micro-pillars. The sample may be bound to the porous material 20a in order to quantitatively weigh the sample.

Further, a reagent which is capable of reacting with the sample may be bound to a surface of the porous material 20a. The resulting product is defined as a label conjugate. The label conjugate refers to a material that specifically reacts with the sample. Various types of label conjugates may be used, according to the sample. By way of example, when a material to be analyzed as the sample is antibody A, the label conjugate may be a conjugate, such as an antigen or an antibody previously linked with the label material, such as, for example, a fluorescent material.

By way of example, as the label material, a label in the label conjugate may include any one or more of latex beads, metal colloids such as gold colloid and silver colloid, enzymes such as peroxidases, fluorescent materials, luminous materials, super-paramagnetic materials, materials including a Lanthanoid (III) chelate, and/or radioisotopes, but the exemplary embodiments are not limited thereto.

The analysis unit 100a may further include an accommodation chamber 14 configured to accommodate a sample so as to prevent the sample from overflowing from the quantitative reaction chamber 20. The accommodation chamber 14 may be disposed closer to the center of the platform 4 than the quantitative reaction chamber 20. This arrangement is configured to accommodate a remaining amount of the sample after the sample is quantified in the quantitative reaction chamber 20. The sample which remains after the sample is quantified in the quantitative reaction chamber 20 may be accommodated into the accommodation chamber 14.

The analysis unit 100a may further include a first waste chamber 13 which is configured to accommodate the sample present inside the accommodation chamber 14 and the sample present in the channel. The first waste chamber 13 may be disposed farther from the center of the platform 4 than the quantitative reaction chamber 20.

The analysis unit 100a may further include a separate reaction chamber 21 in addition to the quantitative reaction chamber 20. The separate reaction chamber 21 may be used when a secondary reaction is needed, and may be used to wash the sample which has moved from the quantitative reaction chamber 20. For this purpose, the separate reaction chamber 21 may include one or more buffer chambers 15a, 15b, and 15c, which are bound to the reaction chamber 21. A buffer solution for washing the reacted sample or a reagent required for secondary reactions may be accommodated into the buffer chambers 15a, 15b and 15c.

The reacted reagent is transferred to the detection chamber 23 for detection of the sample. Photodectection using a light source (not shown) configured to radiate light and a light sensor (not shown) configured to receive the radiated light may be performed in the detection chamber 23. In this case, the microfluidic device may include a separate light blocking portion 23a, because detection errors may occur when external light separately enters the detection chamber 23.

The microfluidic device may further include a contaminant accommodation chamber 22 configured to prevent contaminants from being accommodated into the detection chamber 23 so as to prevent an occurrence of errors in detection of the sample in the detection chamber 23. The sample may flow into the detection chamber 23 via the contaminant accommodation chamber 22. In addition, the microfluidic device may further include a second waste chamber 24 which is used to accommodate an overflow of the sample which occurs after the detection chamber 23 is filled. Each chamber is configured so that the sample can sequentially move from the contaminant accommodation chamber 22 to the detection chamber 23, and then from the detection chamber 23 to the second waste chamber 24. These chambers will be described below.

Further, the microfluidic device 1 may further include valves 30 provided at a channel which connects the chambers to each other. Each of the valves 30 may include any one or more of various types of valves such as valves (for example, capillary valves) which are passively opened when a pressure higher than a certain pressure is applied, and/or valves which are actively switched when power or energy is applied from the outside by actuation signals. The microfluidic device 1, according to an exemplary embodiment, employs phase transition valves which are switched by absorbing energy from the outside.

Each of the valves 30 is disposed in a two-dimensional array or a three-dimensional array between the first substrate 2 and the second substrate 3 constituting the platform 4 in order to interrupt the flow of a fluid, and each valve 30 melts at a relatively high temperature in order to facilitate movement of the fluid to an adjacent available space, thereby opening channels.

To apply heat to the valves 30, an external energy source (not shown) configured to emit light may be disposed outside the platform 4. The valves 30 may be opened when the external energy source (not shown) emits light toward the valves 30.

Each of the valves 30 may be composed of a phase transition material, and exothermic particles may be dispersed in the phase transition material. The exothermic particles may have a size such that the exothermic particles can freely move in the channels, which have a width which falls within a range of between several hundreds of micrometers and several thousands of micrometers (μm). The exothermic particles have an exothermic property according to which the temperature rapidly increases and heat is generated by energy of light (for example, laser beams) when the exothermic particles are irradiated with the light. To exhibit such property, the exothermic particles may have a structure which includes a core which has a metal component and a shell which exhibits hydrophobicity. For example, the exothermic particles may have a structure which includes a core made of iron (Fe) and a shell which is made of a plurality of surfactants which are bound to the Fe so as to surround the core. Commercially available materials currently dispersed in a carrier oil may be used as the exothermic particles.

The phase transition material may include at least one of a wax, a gel and a thermoplastic resin.

The phase transition material may be wax. When light energy absorbed by the exothermic particles is transferred to the vicinity of wax in the form of heat energy, the wax melts accordingly to exhibit fluidity. As a result, the valves are collapsed, and the channels are opened. The wax preferably has a proper melting point. When the melting point of the wax is too high, a relatively large amount of time is required until the wax is melted after the commencement of light irradiation, which causes difficulty with respect to precisely controlling an opening point of time. Conversely, when the melting point of the wax is too low, the wax may be partially melted in a state in which the wax is not irradiated with light, thereby resulting in an undesired leakage of a fluid. The wax that may be used herein may include any one or more of paraffin wax, microcrystalline wax, synthetic wax, and/or natural wax.

Further, the phase transition material may be a gel, or a thermoplastic resin. The gel may be made from any one or more of a polyacrylamide, a polyacrylate, a polymetacrylate, or a polyvinylamide. In addition, any one or more of COC, PMMA, PC, PS, POM, PFA, PVC, PP, PEEK, PA, PSU and/or PVDF may be used as the thermoplastic resin.

According to an exemplary embodiment, the microfluidic device may also further include bent holes 16a, 16b, 16c and 25a which extend from chambers and which carry air so as to promote the flow of air.

Figure 5:
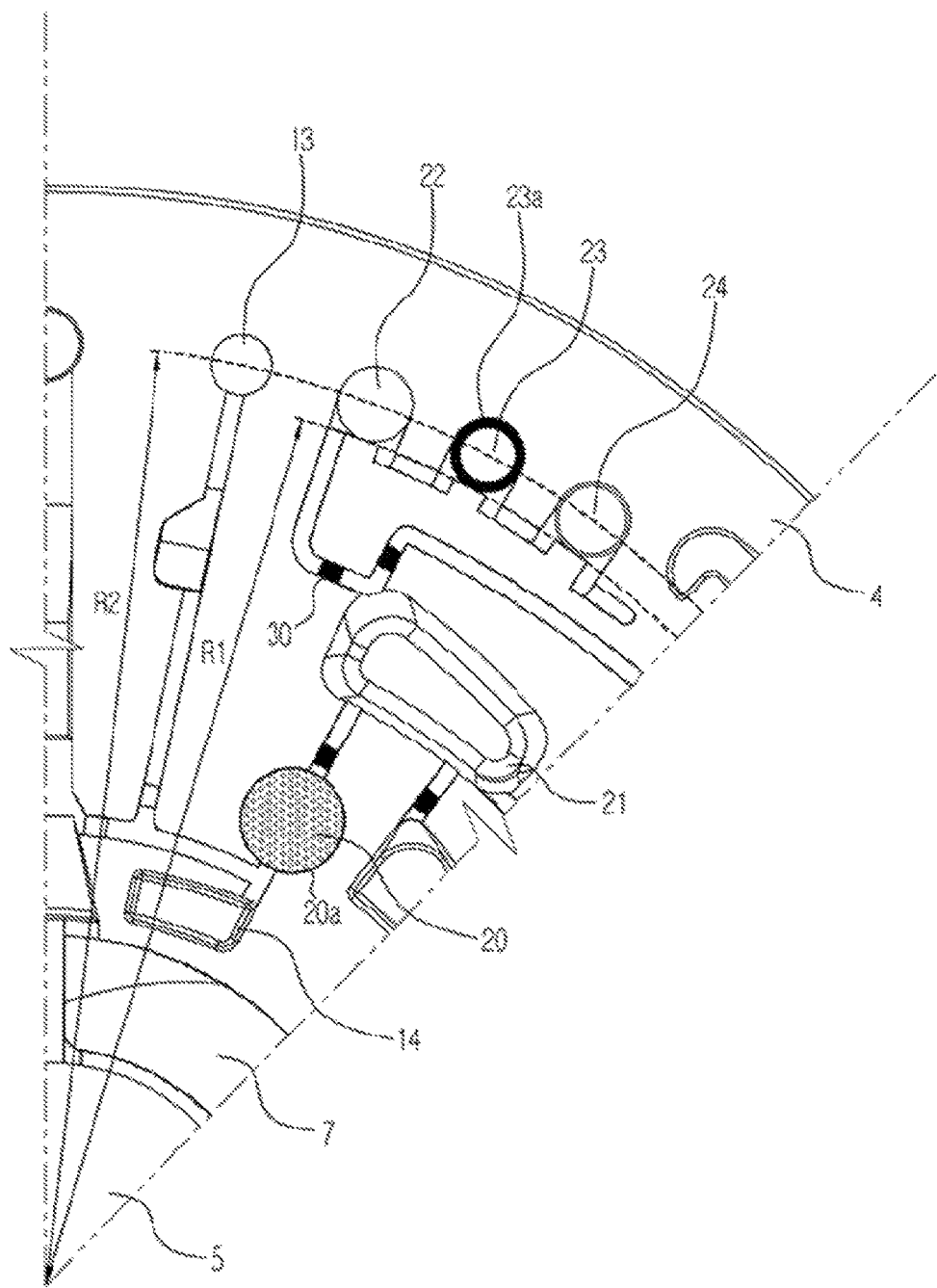
FIG. 5 is a diagram showing a concave portion of the microfluidic device, according to one exemplary embodiment.
Figure 6:
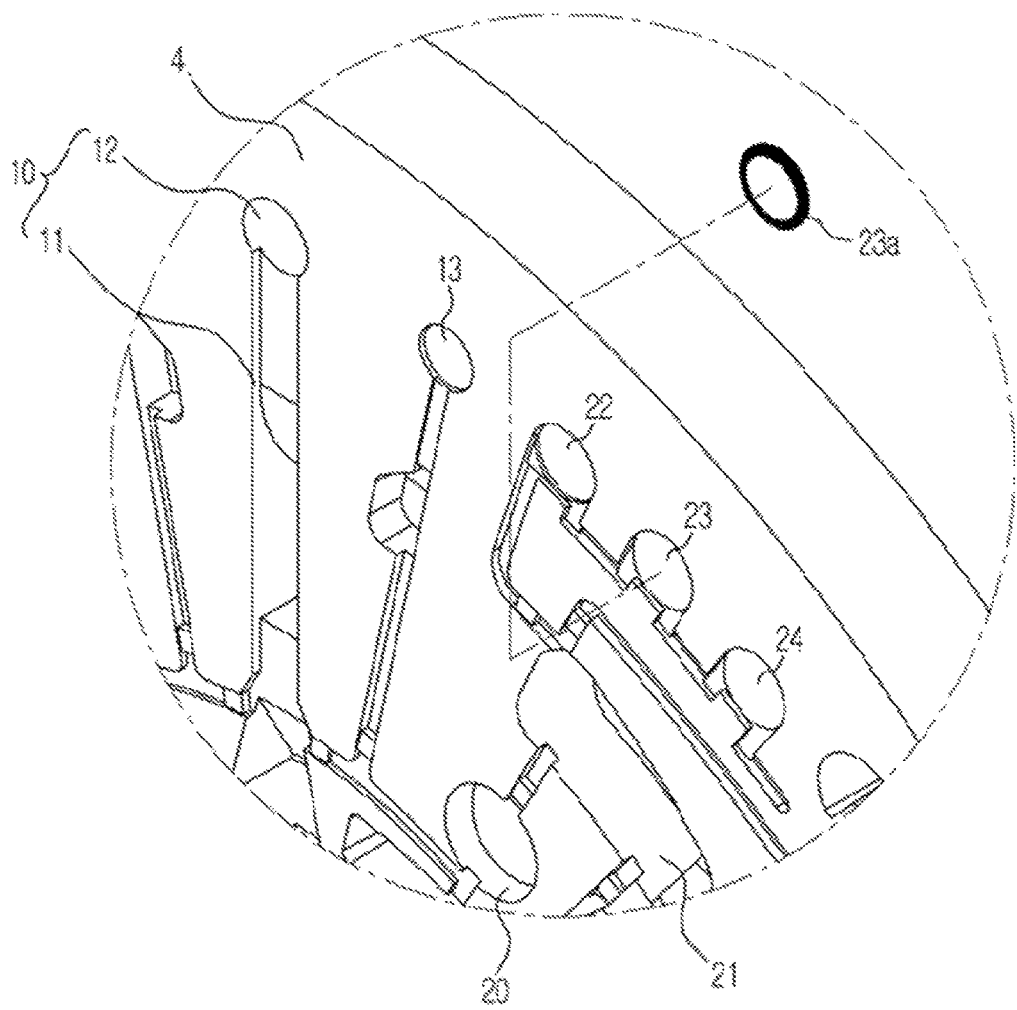
FIG. 6 is an exploded diagram showing a light blocking portion of the microfluidic device, according to one exemplary embodiment.

FIG. 5 is a diagram showing a concave portion of the microfluidic device according to an exemplary embodiment, and FIG. 6 is an exploded diagram showing a light blocking portion of the microfluidic device according to an exemplary embodiment.

As shown in FIGS. 5 and 6, a separate light blocking portion 23a may be provided at the detection chamber 23. Photodectection using a light source (not shown) configured to radiate light and a light sensor (not shown) configured to receive the radiated light may be performed in the detection chamber 23. In this case, the microfluidic device may include a separate light blocking portion 23a, because detection errors may occur when external light separately enters the detection chamber 23. The light blocking portion 23a may be arranged so as to surround an outer wall of the detection chamber 23. The light blocking portion 23a may be formed of a material which is impenetrable by light. By way of example, the light blocking portion 23a may be formed of a plastic material or a rubber material. In addition, a portion of the microfluidic device may be directly printed with opaque colors, and may be used as the light blocking portion 23a.

Contaminants may be generated by reaction of the sample with the reagent during an inspection process. According to an exemplary embodiment, the contaminant may also be generated according to application of the phase transition valve, since the phase transition valves configured to absorb light energy from the outside in order to open the channels are employed. Such contaminants are accommodated into the contaminant accommodation chamber 22.

The contaminant accommodation chamber 22 may include an inlet port which is configured to facilitate a flow of the sample into the contaminant accommodation chamber 22, and an outlet port which is configured to facilitate a flow of the sample out from the contaminant accommodation chamber 22 and into the detection chamber 23. According to an exemplary embodiment, the outlet port and a central region 5 of the platform 4 may be provided such that the distance R1 between the outlet port and the central region 5 of the platform 4 is shorter than the distance R2 between the center of the contaminant accommodation chamber 22 and the central region 5 of the platform 4. The contaminants are positioned farther from the central region 5 than the distance R2, because a centrifugal force is applied to the contaminants due to their mass. Therefore, because the contaminants do not move to within a distance of R1 with respect to the central region 5 while the microfluidic device 1 rotates, the contaminants may not move to the detection chamber 23 via the outlet port, and may be accommodated into the contaminant accommodation chamber 22.

Similarly, the inlet port and the central region 5 of the platform 4 may be provided such that the distance R1 between the inlet port and the central region 5 of the platform 4 is shorter than the distance R2 between the center of the contaminant accommodation chamber 22 and the central region 5 of the platform 4. As described above, the contaminants may be prevented from flowing backward into the reaction chambers 20 and 21 via the inlet port while the microfluidic device 1 rotates.

According to an exemplary embodiment, the microfluidic device includes the light blocking portion configured to prevent an occurrence of detection errors which might otherwise be caused in the detection chamber, and thus can be useful for the purpose of preventing the occurrence of detection errors which could be caused by interference of external light.

According to another exemplary embodiment, the microfluidic device also includes the quantitative reaction chamber configured to facilitate the simultaneous weighing and reaction of the sample, and thus can be useful for the purposes of reducing an inspection time and miniaturizing microfluidic devices.

According to still another exemplary embodiment, the microfluidic device also includes the contaminant accommodation chamber, and thus may be useful for the purpose of preventing contaminants from entering the detection chamber.

Although a few exemplary embodiments have been shown and described, it will be appreciated by those skilled in the art that changes may be made in these exemplary embodiments without departing from the principles and spirit of the present inventive concept, the scope of which is defined in the claims and their equivalents.

What is claimed is:

1. A microfluidic device comprising:
a platform;
a plurality of chambers, including a first chamber which is provided in the platform and configured to accommodate a sample, and at least a second chamber; and
at least one channel configured to couple the first chamber to the at least the second chamber,
wherein the plurality of chambers further comprises:
a reaction chamber in which a reaction of the sample occurs;
a contaminant accommodation chamber configured to accommodate contaminants generated as a result of the reaction of the sample in the reaction chamber; and
a detection chamber configured to detect the sample,
wherein the contaminant accommodation chamber comprises an inlet port configured to facilitate a flow of the sample into the contaminant accommodation chamber, and an outlet port configured to facilitate a flow of the sample out from the contaminant accommodation chamber and into the detection chamber, and
the inlet port and the outlet port are spaced apart from each other, and
a linear distance between the outlet port and a central point of the platform is shorter than a linear distance between a center of the contaminant accommodation chamber and the central point of the platform.

2. The microfluidic device of claim 1, wherein the sample moves via the at least one channel among the reaction chamber, the contaminant accommodation chamber, and the detection chamber.

3. The microfluidic device of claim 1, wherein a linear distance between the inlet port and the central point of the platform is shorter than a linear distance between a center of the contaminant accommodation chamber and the central point of the platform.

4. The microfluidic device of claim 1, further comprising a light blocking portion configured to surround an outer wall of the detection chamber so as to prevent an occurrence of at least one error which relates to a detection of the sample in the detection chamber.

5. The microfluidic device of claim 1, further comprising a valve provided on the at least one channel, wherein the valve includes phase transition material and exothermic particles dispersed in the phase transition material.

6. The microfluidic device of claim 5, wherein the phase transition material includes at least one of a wax, a gel and a thermoplastic resin.

7. The microfluidic device of claim 1, wherein the first chamber, the second chamber, and the reaction chamber are all closer to the central point of the platform than the contaminant accommodation chamber.

* * * * *